United States Patent
Menn (10) Patent No.: US 10,201,353 B2
(45) Date of Patent: Feb. 12, 2019

(54) LIGATION CLIP

(71) Applicant: Pavel Menn, Marblehead, MA (US)

(72) Inventor: Pavel Menn, Marblehead, MA (US)

( * ) Notice: Subject to any disclaimer, the term of this patent is extended or adjusted under 35 U.S.C. 154(b) by 0 days.

(21) Appl. No.: 15/424,241

(22) Filed: Feb. 3, 2017

(65) Prior Publication Data
US 2018/0221029 A1 Aug. 9, 2018

(51) Int. Cl.
*A61B 17/12* (2006.01)
*A61B 17/122* (2006.01)

(52) U.S. Cl.
CPC ............ *A61B 17/122* (2013.01); *A61B 17/12* (2013.01)

(58) Field of Classification Search
CPC .... A61B 17/122; A61B 17/1227; A61B 17/12
See application file for complete search history.

(56) References Cited

U.S. PATENT DOCUMENTS

| | | | |
|---|---|---|---|
| 3,363,628 A * | 1/1968 | Wood .................... | A61B 17/122 206/339 |
| 3,631,707 A * | 1/1972 | Miller .................. | A61B 17/122 606/142 |
| 3,867,944 A * | 2/1975 | Samuels ............... | A61B 17/122 24/23 W |
| 4,188,953 A | 2/1980 | Klieman et al. | |
| 4,519,392 A | 5/1985 | Lingua | |
| 4,667,671 A | 5/1987 | Danzig | |
| 4,702,247 A * | 10/1987 | Blake, III ............ | A61B 17/122 606/157 |
| 4,834,096 A | 5/1989 | Oh et al. | |
| 4,844,066 A | 7/1989 | Stein | |
| 4,976,722 A * | 12/1990 | Failla ................... | A61B 17/122 606/151 |
| 4,979,950 A * | 12/1990 | Transue ............... | A61B 17/122 606/158 |
| 5,171,253 A | 12/1992 | Klieman | |
| 5,201,746 A * | 4/1993 | Shichman ............ | A61B 17/122 227/902 |
| 5,201,900 A | 4/1993 | Nardella | |

(Continued)

FOREIGN PATENT DOCUMENTS

WO 1997047245 A1 12/1997

OTHER PUBLICATIONS

Symmetry Surgical, Vesocclude Medical, Ligating Clips, http://symmetrysurgical.com/Welcome/Default.aspx?scenarioID=65000086.

(Continued)

*Primary Examiner* — Shaun David
(74) *Attorney, Agent, or Firm* — Daniel N. Smith (57) ABSTRACT

The ligation clip includes opposing legs connected at a connection point at which the clip pivots to the clamped position on a vessel. The entire clip has a completely semi-circular outside surface. The inside vessel engaging surfaces of the legs of the clip have a unique vessel retaining system that includes a plurality of rounded protrusions alternating with rounded depressions. The retaining system is positioned "within" the inside vessel engaging surfaces of the legs such that a flat surface remains adjacent to our around the retaining system. In addition, there are no sharp edges associated with the ligation clip. All transition points between the outer and inner surfaces of the clip are rounded to prevent any sharp edges.

9 Claims, 6 Drawing Sheets

(56) References Cited

U.S. PATENT DOCUMENTS

| | | | | |
|---|---|---|---|---|
| 5,269,792 | A | 12/1993 | Kovac et al. | |
| 5,509,920 | A * | 4/1996 | Phillips | A61B 17/122 227/902 |
| 5,501,693 | A | 5/1996 | Gravener | |
| 5,609,599 | A | 3/1997 | Levin | |
| 5,620,452 | A | 4/1997 | Yoon | |
| 5,626,592 | A | 5/1997 | Phillips et al. | |
| 5,713,911 | A | 2/1998 | Racenet et al. | |
| 5,843,101 | A | 12/1998 | Fry | |
| 6,015,417 | A * | 1/2000 | Reynolds, Jr. | A61B 17/064 606/151 |
| 6,193,732 | B1 | 2/2001 | Frantzen et al. | |
| 6,306,150 | B1 | 10/2001 | Levinson | |
| 6,537,289 | B1 * | 3/2003 | Kayan | A61B 17/122 606/157 |
| 6,610,073 | B1 | 8/2003 | Levinson | |
| 6,849,078 | B2 * | 2/2005 | Durgin | A61B 17/10 606/142 |
| 7,316,693 | B2 | 1/2008 | Viola | |
| 7,338,503 | B2 | 3/2008 | Rosenberg et al. | |
| 7,699,860 | B2 | 4/2010 | Huitema et al. | |
| 7,896,895 | B2 | 3/2011 | Boudreaux et al. | |
| 8,100,926 | B1 | 1/2012 | Filshie et al. | |
| 8,262,679 | B2 | 9/2012 | Nguyen | |
| 8,556,920 | B2 | 10/2013 | Huitema et al. | |
| 8,998,935 | B2 | 4/2015 | Hart | |
| 9,282,972 | B1 | 3/2016 | Patel et al. | |
| 9,445,820 | B2 | 9/2016 | Whiting | |
| 9,456,824 | B2 | 10/2016 | Willett et al. | |
| 9,517,064 | B2 | 12/2016 | Sarradon | |
| 9,642,627 | B2 * | 5/2017 | Zammataro | A61B 17/1285 |
| 9,730,752 | B2 | 8/2017 | Keller | |
| 2005/0256529 | A1 | 11/2005 | Yawata et al. | |
| 2005/0273122 | A1 * | 12/2005 | Theroux | A61B 17/122 606/157 |
| 2006/0235468 | A1 * | 10/2006 | Huitema | A61B 17/064 606/219 |
| 2008/0312670 | A1 * | 12/2008 | Lutze | A61B 17/122 606/157 |
| 2011/0224701 | A1 * | 9/2011 | Menn | A61B 17/122 606/151 |
| 2011/0270285 | A1 * | 11/2011 | Lissa | A61B 17/122 606/151 |
| 2011/0295290 | A1 * | 12/2011 | Whitfield | A61B 17/122 606/158 |
| 2014/0018830 | A1 | 1/2014 | Shelton, IV | |
| 2014/0171986 | A1 * | 6/2014 | Shelton, IV | A61B 17/122 606/157 |
| 2014/0243862 | A1 | 8/2014 | Bagaoisan et al. | |
| 2015/0272588 | A1 | 10/2015 | Khan | |
| 2017/0189714 | A1 * | 7/2017 | Racenet | A61N 5/1007 |
| 2018/0185029 | A1 * | 7/2018 | Lebens, III | A61B 17/122 |

OTHER PUBLICATIONS

Formation Design Group, Jenkins Clinic Ligation Clip, http://gallery.wacom.com/gallery19031959/Jenkins-Clinic-Ligation-Clip.

Aseculap USA, Laparoscopic Appliers, https://www.aesculapusa.com/products/surgical-instruments/laparoscopy/ligation.

* cited by examiner

LIGATION CLIP

BACKGROUND

Technical Field

The present principles relate to surgical clips. More particularly, it relates ligation clips having no sharp edges, rounded protrusions and a particular implementation of the protrusions and surrounding surfaces that provide for easy, atraumatic removal of the clip from a vessel after use.

Related Art

A wide number of surgical procedures employ surgical clips (i.e., ligation clips). Such surgical procedures may require vessels, organs or other tissues of the human body to be ligated. Surgical clips ligate, clamp, close off or otherwise occlude the engaged portion of the clamped vessels, organs or other tissues in a surgical site. Such clips may also be used to secure the ends of a suture, as in place of a conventional suture knot.

Ligation can be performed with a ligating clip (i.e., a surgical clip) or by suturing with surgical thread. Suturing requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. So long as the clips and applicator are designed with endoscopic procedures in mind, they are a preferred choice.

The clips are often in the form of thin, narrow, metal or polymeric U-shaped or V-shaped members that are placed over the vessel, tissue or suture material and then forced into a closed position using a clip applicator. Clips constructed of metal, may be initially open and then permanently deformed into a closed or clamped configuration around the desired blood vessel or other tissue structure using an appropriate clip applicator.

The clips of the prior art suffer from various drawbacks. One example of such drawbacks includes a full mesh of opposing teeth or clip protrusions. When the clip is closed on a vessel, a full mess of opposing teeth or clip protrusions not only can puncture or damage the vessel upon application to the vessel, but they also cannot be removed by sliding the closed clip off the vessel (due to the complete mesh design), and often require a separate removal tool or process.

Another example of a drawback of the clips of the prior art is the sharp edges included anywhere on the same. As is appreciated by those of skill in the art, a sharp edge or corner between surfaces of the clip itself can be a cause of other tissue damage surrounding the vessel, and/or the vessel itself either while it is being applied, or after application to the vessel.

The present principles are directed to providing an improved ligation clip that overcomes the above-noted problems and solving one or more of the needs as set forth above.

SUMMARY

According to an implementation, the ligation clip includes a first leg having a distal end and a proximal end, a second leg having a distal end and a proximal end, and a connection point where the proximal ends of each leg meets. The first and second legs each have an inside flat surface. A retaining system is positioned within each of the flat surfaces such that a portion of the inside flat surfaces remains flat adjacent the retaining system.

According to another implementation, the ligation clip includes a first leg having a distal end and a proximal end, a second leg having a distal end and a proximal end, and a connection point where the proximal ends of each leg meets. The first leg, second leg and connection point all have a semi-circular cross section of a predetermined radius The first and second legs each having an inside vessel engaging surface. A plurality of alternating rounded protrusions are disposed on the vessel engaging surfaces of each the first and second leg and are separated by a plurality of alternating rounded depressions.

According to yet a further implementation, the ligation clip includes a first leg having a distal end and a proximal end, a second leg having a distal end and a proximal end, and a connection point where the proximal ends of each leg meets. The first and second legs each having an inside vessel engaging surface. A plurality of alternating rounded protrusions are disposed on the vessel engaging surfaces of each the first and second leg and are separated by a plurality of alternating rounded depressions. The protrusions of the first leg do not mesh into the protrusions of the second leg when the clip is in a clamped or closed position.

These and other aspects, features and advantages of the present principles will become apparent from the following detailed description of exemplary embodiments, which is to be read in connection with the accompanying drawings.

BRIEF DESCRIPTION OF THE DRAWINGS

The present principles may be better understood in accordance with the following exemplary figures, in which.

DETAILED DESCRIPTION

The present principles are directed to surgical or ligation clips.

The present description illustrates the present principles. It will thus be appreciated that those skilled in the art will be able to devise various arrangements that, although not explicitly described or shown herein, embody the present principles and are included within its spirit and scope.

All examples and conditional language recited herein are intended for pedagogical purposes to aid the reader in understanding the present principles and the concepts contributed by the inventor(s) to furthering the art, and are to be construed as being without limitation to such specifically recited examples and conditions.

Moreover, all statements herein reciting principles, aspects, and embodiments of the present principles, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Reference in the specification to "one embodiment", "an embodiment" or :"an implementation" of the present principles, as well as other variations thereof, means that a particular feature, structure, characteristic, and so forth described in connection with the embodiment is included in at least one embodiment of the present principles. Thus, the appearances of the phrase "in one embodiment", "in an embodiment", or "an implementation" as well any other variations, appearing in various places throughout the specification are not necessarily all referring to the same embodiment.

Figure 1A:
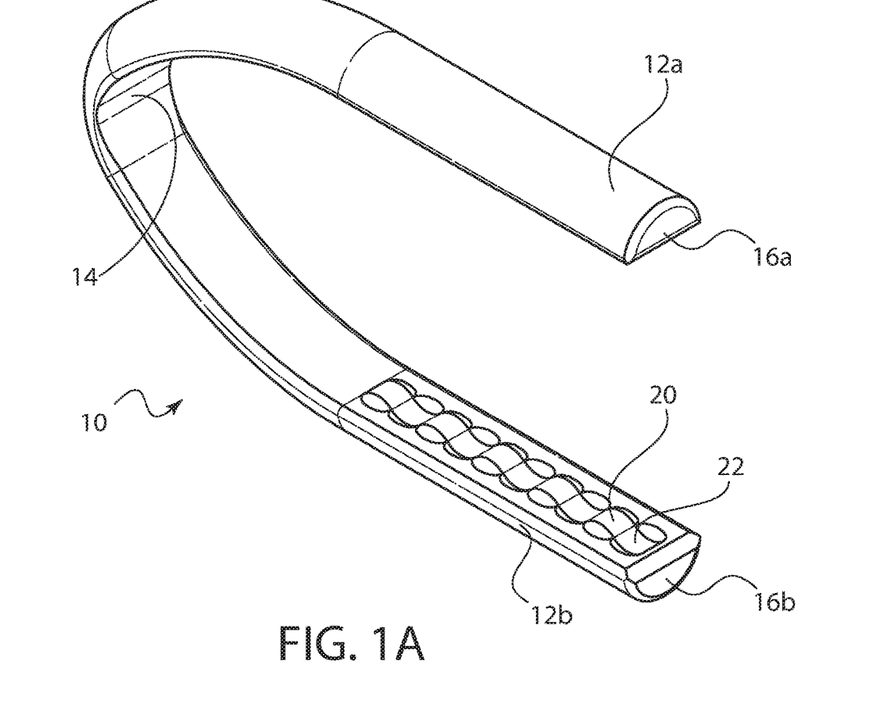
FIG. 1A is perspective view of the ligation clip in an open, un-applied state, according to an implementation of the present principles.
Figure 1B:
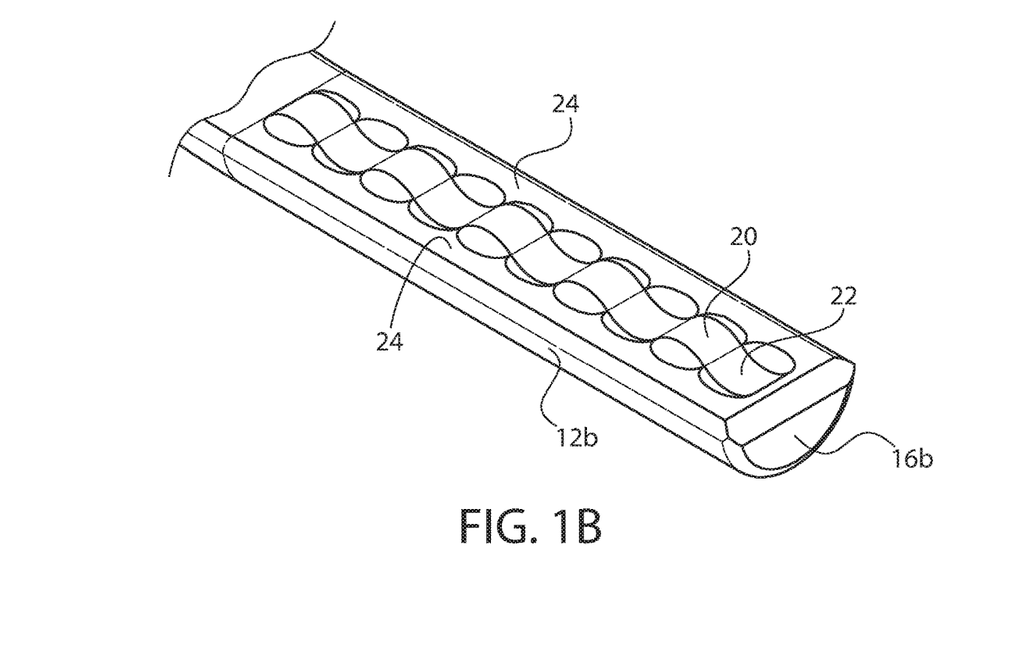
FIG. 1B is an enlarged view of one side of the vessel engaging portion of the ligation clip, according to an implementation of the present principles.
Figure 2:
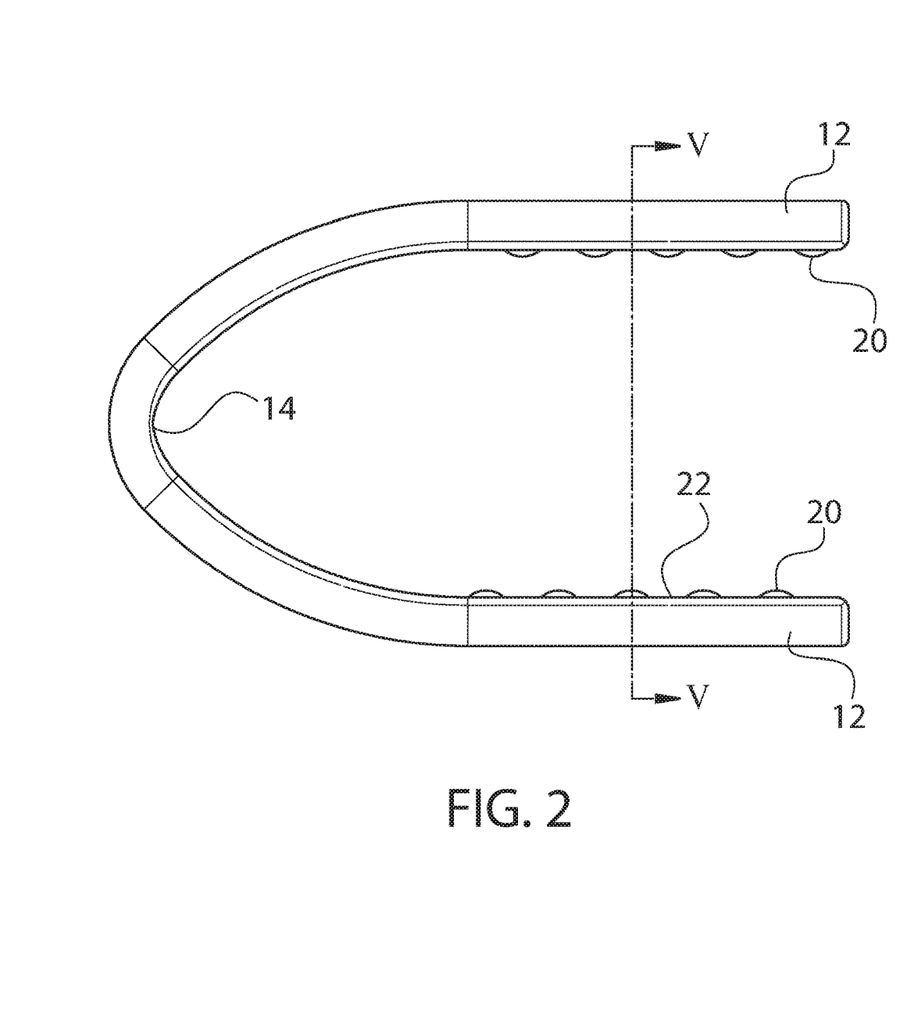
FIG. 2 is a side view of the ligation clip shown in FIG. 1.
Figure 3:
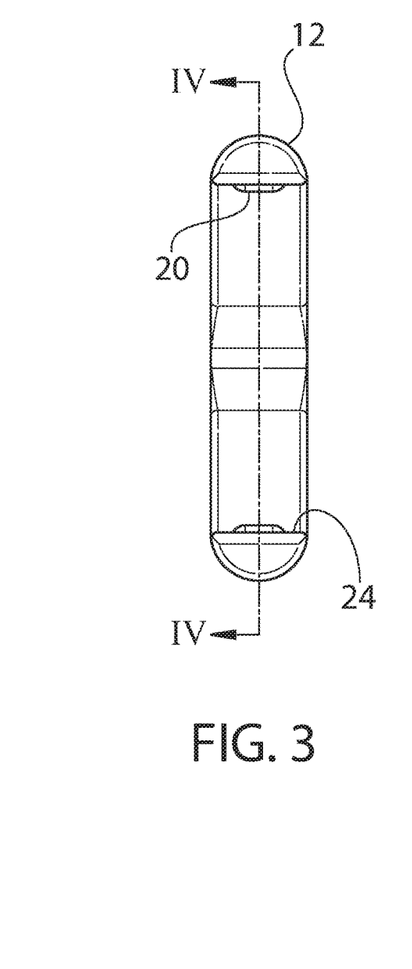
FIG. 3 is a front view of the ligation clip looking into the same, according to an implementation of the present principles.
Figure 4:
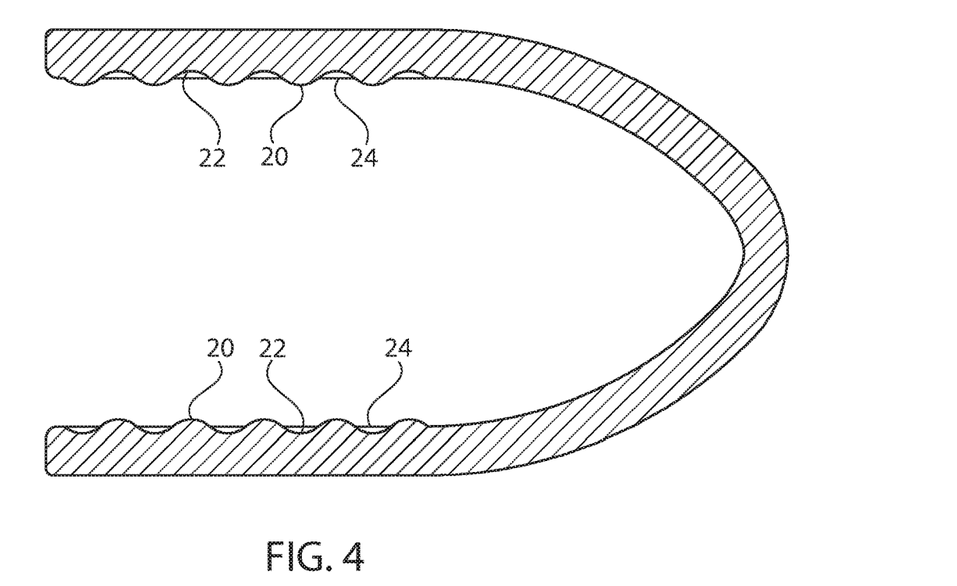
FIG. 4 is a cross-sectional view of the ligation clip of FIG. 3 taken along lines IV-IV, according to an implementation of the present principles.

Referring to FIGS. 1A and 1B, there is shown the ligation clip 10 in its open, un-applied position, according to one implementation of the invention. The clip 10 has opposing legs 12A and 12B each having a distal end 16A and 16B, respectively. The proximal ends of each of the legs 12A and 12B meet at a folding or pivot point 14. According to the present principles, there are various improvements which will be discussed separately below, but as will be appreciated by those of skill in the art, these various improvements can be implemented individually, and when implemented together all work to provide a new ligation clip that not only provides an increased performance in the clamping of a vessel, but is safer during both the application and removal processes.

Figure 5:
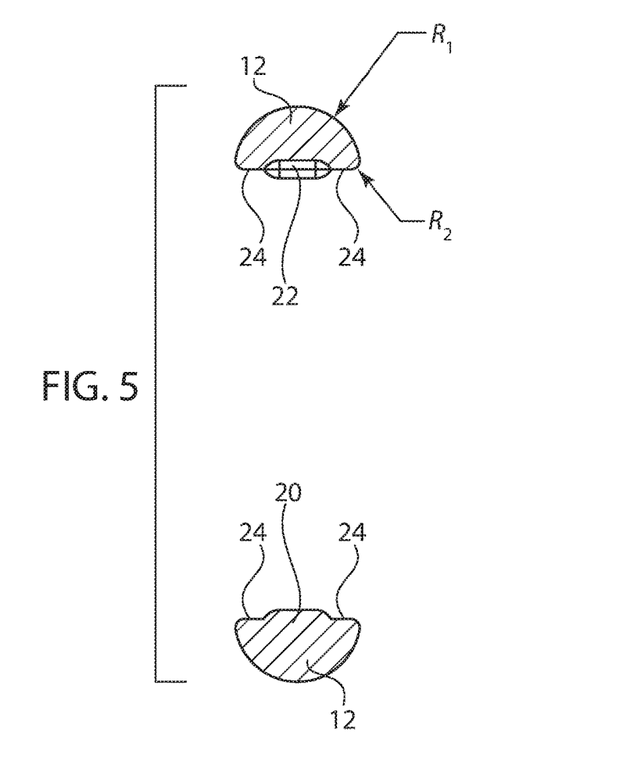
FIG. 5 is an enlarged cross-sectional view of the ligation clip of FIG. 2 taken along lines V-V, showing the radiused edges according to an implementation of the present principles.

According to one preferred implementation, the entire clip 10 is semi-circular in cross section and does not include any sharp edges or transitions. This can best be seen in FIGS. 1A, 3, 5 and 7. Referring more specifically to the cross sectional view of FIG. 5, the clip 10 has radius R1 that defines the semi-circular cross section of the outer surface of entire clip. In addition, all transition edges of the clip are rounded as well (e.g., all transitions from the outer surface to all of the inside surfaces), indicated for example by radius R2. In one implementation, radius R1 can be, for example 0.021 inches ±0.006 inches. Radius R2 can be, for example, 0.003 inches, or in a range of 0.003-0.006 inches. These radiuses are chosen to be sufficient enough so as to not cause necrosis of the vessel, or severing of the vessel (i.e. scissoring) when the clip is applied at an angle relative to the vessel.

Those of skill in the art will appreciate that by providing a semi-circular cross section design of the clip, in combination with the rounding of every transition edge thereof, there will be no sharp edges or points that could otherwise cause tissue damage once inserted and used inside a patient.

According to another preferred implementation, each of the legs 12 have a flat inside surface 24 (FIGS. 1B, 3, 4, 5, 8) which can also be referred to as the "vessel engaging surface". This inside surface 24 is where the vessel retaining system of the clip is positioned. According to this implementation, by positioning the retaining system of the clip within or inside the flat surface 24, there can be no groove, slot, depression or protrusion that extends laterally across the entire vessel engaging surface of the clip.

The retaining system of the clip is made up of rounded protrusions 20 and rounded depressions 22. The rounded protrusions 22 are alternatingly placed within the flat surface 24 of the respective leg 12. Rounded depressions 22 are positioned between each of the rounded protrusions 20. When the clip 10 is closed onto a vessel (as will be described in more detail below), the rounded protrusions 22 of leg 12A are oppositely aligned with the rounded depressions 20 of the opposing leg 12B, and vice versa. According to one exemplary implementation, the rounded protrusions 20 have a radius of 0.012 inch. According to one preferred implementation, the height of the protrusions can range from 0.003-0.006 inches, in order to maintain the a-traumatic removal of the same.

Figure 6A:
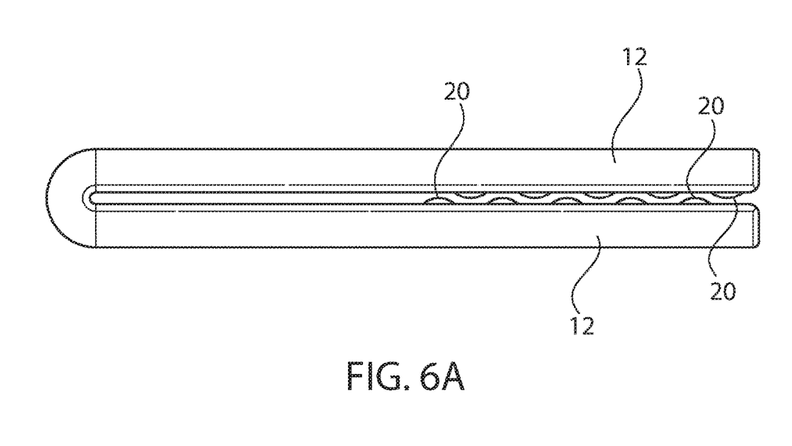
FIG. 6A is a side view of the ligation clip in the closed position, according to an implementation of the present principles.
Figure 6B:
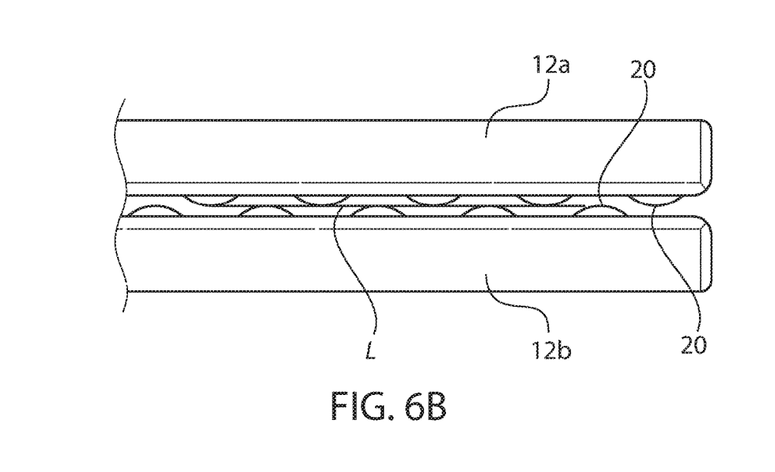
FIG. 6B is an enlarged view of the closed clip depicting the meshing between the opposing protrusions and spaces by the ligated tissue, according to an implementation of the present principles.
Figure 7:
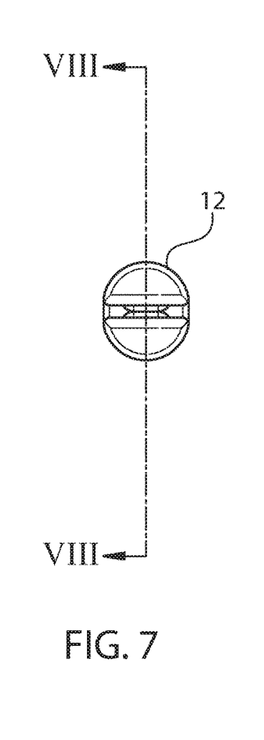
FIG. 7 is an end view of the closed ligation clip of FIG. 6, according to an implementation of the present principles.
Figure 8:
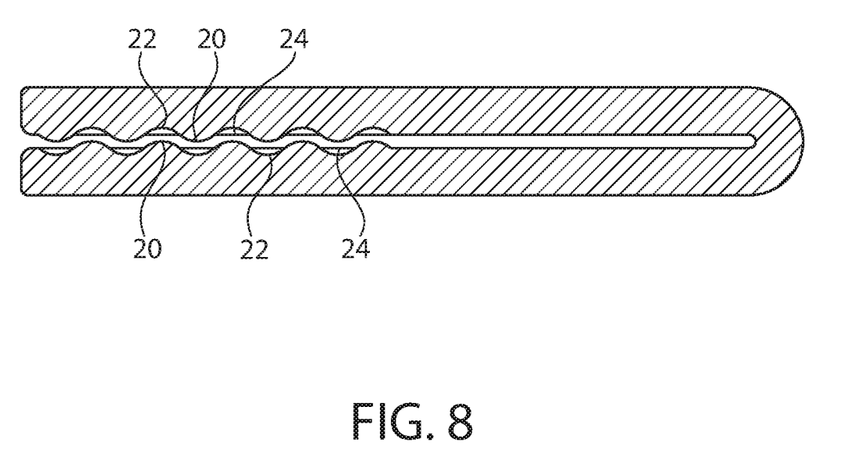
FIG. 8 is a cross-sectional view of the ligation clip of FIG. 7 taken along lines VIII-VIII, according to an implementation of the present principles.

FIGS. 6A, 6B and 8 show a side view, and cross-sectional view, respectively, of the clip 10 where the alternating arrangement of the protrusions 20 and depressions 24 is more readily understood. Note that the protrusions 20 do not mesh with their corresponding depression 22 on the opposing leg (i.e., protrusion 22 does not enter the opposing depression 20). As shown more clearly in FIGS. 6B & 7, the protrusions 22 on opposing legs do not mesh with the opposing depressions. In fact, the uppermost portion of the protrusions 22 one leg 12A line up uppermost portion of the protrusions 22 of the opposing leg 12B. This is depicted by the line L added to FIG. 6B showing that the protrusions 22 do not mesh at all in between the opposing protrusions, or into the corresponding depression 20.

Referring to FIG. 8, it can be seen that the flat surfaces 24 around the protrusions 20 and depressions 22 that do not mesh into each other clearly assists in the clamping of the vessel when the clip is close as shown. In fact, this design of the protrusions and depressions along with the flat surfaces enable utilize the vessel for meshing. This meshing, coupled with the rounded surfaces of the protrusions 20 and the depressions, and the flat surfaces 24 surrounding the protrusions and depressions, allow for increased stability and retention of the clip on the tissue (vessel) while allowing for "atraumatic" or Non-traumatic removal of the clip from the vessel by sliding the clip off the vessel. In other words, the removal of the clip from the vessel does not cause any damage to the vessel and/or the surrounding tissue as a result of these rounded surfaces.

Figure 9:
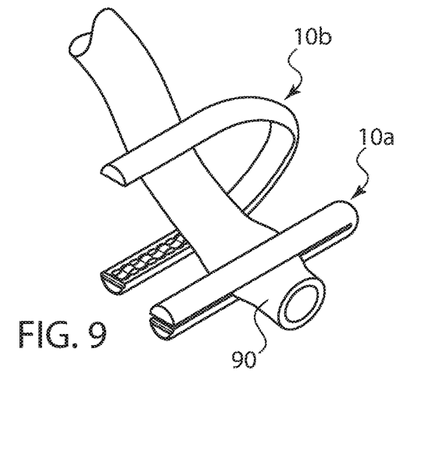
FIG. 9 is a diagrammatic view of the application of the ligation clip to a vessel, according to an implementation of the present principles.
Figure 10:
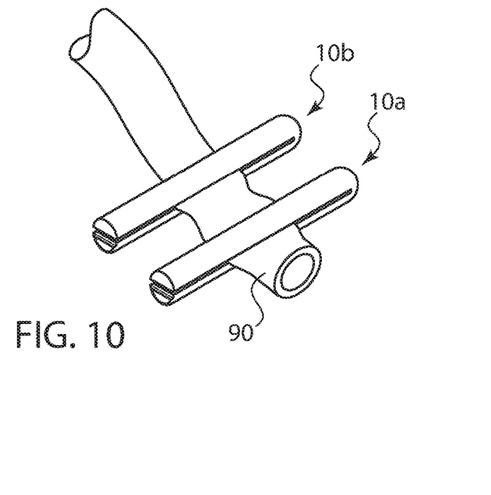
FIG. 10 is a diagrammatic view of the application of the ligation clip to a vessel, according to an implementation of the present principles.
Figure 11A:
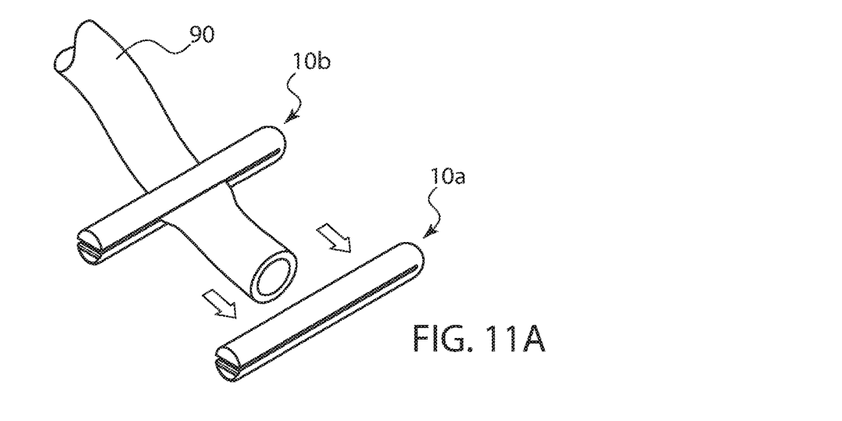
FIG. 11A is a diagrammatic view of the removal of the ligation clip by sliding in the direction of the cut, according to an implementation of the present principles.
Figure 11B:
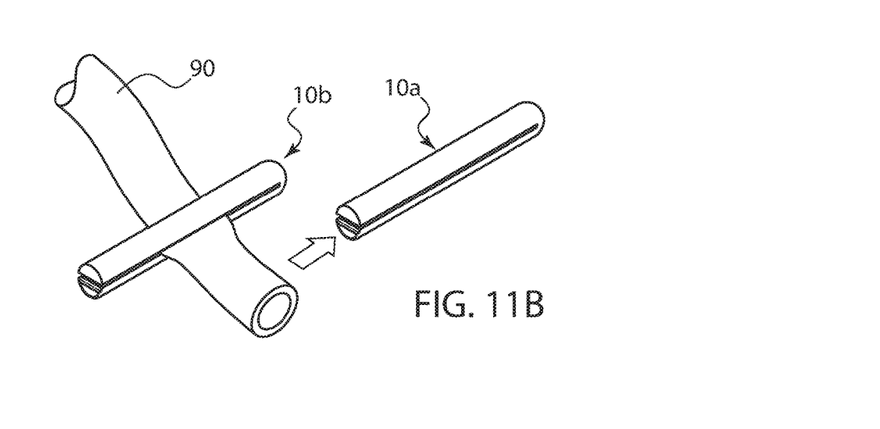
FIG. 11B is a diagrammatic view of the removal of the ligation clip by sliding in a direction transverse to the vessel, according to an implementation of the present principles.

Referring to FIGS. 9-11, there is shown the stages of operation of the clip 10 according to an implementation of the present principles. Initially, a first clip 10A is applied to a vessel 90. The vessel may then be cut, as shown, or before such cutting, a second clip 10B can be applied to the vessel 90. Those of skill in the art will appreciate that the number of clips using during any procedure can be different, and these images are for exemplary purposes only. In addition, those of skill in the art will also appreciate that these clips are so small that specialized "clip appliers" are used during the surgical procedures, usually under magnification due to the small size of the clips. FIG. 10 shows the vessel 90 with 2 clips applied.

Referring to FIGS. 11a and 11b, one advantageous aspect of the ligation clips of the present principles is the ability to remove the same from the vessel by simply sliding the same off in the direction of the cut (11a) or more preferably in a direction transverse to the vessel 90 (11b). Through the use of the rounded protrusions 20, rounded depressions 22, and the flat surfaces 24, along with the radiused edges of the clip, the sliding of clip 10A off the vessel 90 (in either direction) can be performed "atraumatically", or without trauma or damage to the vessel. Those of skill in the art will further appreciate that a hemostat or other temporary vessel clamp would be used to allow for the removal of the remaining clip 10B, while the vessel is reattached to where it needs to be.

Although the illustrative embodiments have been described herein with reference to the accompanying drawings, it is to be understood that the present principles is not limited to those precise embodiments, and that various changes and modifications may be effected therein by one of ordinary skill in the pertinent art without departing from the scope or spirit of the present principles. All such changes and modifications are intended to be included within the scope of the present principles as set forth in the appended claims.

What is claimed is:

1. A ligation clip comprising;
a first leg having a distal end and a proximal end, said first leg having an inside flat surface;
a second leg having a distal end and a proximal end; said second leg having an inside flat surface;
a connection point where the proximal ends of each leg meet; and
a retaining system positioned within each of the flat surfaces such that a portion of the inside flat surfaces remains flat adjacent the retaining system, the retaining system comprising:
a plurality of rounded protrusions disposed within the inside flat surfaces of each the first and second leg; and
a rounded depression alternatingly disposed between each of the plurality of rounded protrusions of each the first and second leg such that each rounded depression is in contact with and transitions from or to at least one of the plurality of rounded protrusions,
wherein the plurality of rounded protrusions and the rounded depressions disposed between each rounded protrusion form an unbroken curved surface extending along each leg;
wherein each unbroken curved surface forms an unbroken curved line along a cross section that is parallel with the first leg and the second leg; and
wherein each rounded depression that is in contact with and transitions from or to the rounded protrusion forms an unbroken S-shaped curve along a cross section that is parallel with the first leg and the second leg.

2. The ligation clip of claim 1, wherein said first leg, said second leg and said connection point have a semi-circular cross section having a radius in a range of 0.015-0.027 inches.

3. The ligation clip of claim 1, wherein the rounded protrusions of the first leg do not mesh into the rounded depressions of the second leg when the clip is in a clamped or closed position.

4. The ligation clip of claim 1, further comprising transition edges between an outer surface thereof and multiple inside surfaces including the inside flat surfaces, said transition edges being rounded to a radius in a range of 0.003-0.006 inches so as to provide the ligation clip with no sharp edges.

5. A ligation clip comprising;
a first leg having a distal end and a proximal end, said first leg having an inside vessel engaging surface;
a second leg having a distal end and a proximal end; said second leg having an inside vessel engaging surface;
a connection point where the proximal ends of each leg meet; and
a plurality of alternating rounded protrusions arranged within the vessel engaging surfaces of each the first and second leg and being separated by a plurality of alternating rounded depressions such that each rounded depression is in contact with and transitions from or to at least one adjacent rounded protrusion;
wherein the plurality of alternating rounded protrusions and the plurality of alternating rounded depressions form an unbroken curved surface extending along each leg;
wherein each unbroken curved surface forms an unbroken curved line along a cross section that is parallel with the first leg and the second leg;
wherein each rounded depression that is in contact with and transitions from or to the adjacent rounded protrusion forms an unbroken S-shaped curve along a cross section that is parallel with the first leg and the second leg; and
said plurality of alternating rounded protrusions and said plurality of alternating rounded depressions being arranged within the inside vessel engaging surfaces such that a portion of the vessel engaging surfaces remains a flat surface adjacent the protrusions and depressions.

6. The ligation clip of claim 5, further comprising transition edges between an outer surface thereof and multiple inside surfaces including the vessel engaging surface, said transition edges being rounded to a radius in a range of 0.003-0.006 inches so as to provide the ligation clip with no sharp edges.

7. The ligation clip of claim 5, wherein the rounded protrusions of the first leg do not mesh into the rounded depressions of the second leg when the clip is in a clamped or closed position.

8. A ligation clip comprising:
a first leg having a distal end and a proximal end, said first leg having an inside vessel engaging surface;
a second leg having a distal end and a proximal end; said second leg having an inside vessel engaging surface;
a connection point where the proximal ends of each leg meet; and
a plurality of alternating rounded protrusions disposed on the vessel engaging surfaces of each the first and second leg; and
a plurality of alternating rounded depressions positioned between said rounded protrusions such that each rounded depression is in contact with and transitions from or to at least one adjacent rounded protrusion;

wherein the plurality of alternating rounded protrusions and the plurality of alternating rounded depressions form an unbroken curved surface extending along each leg;

wherein each unbroken curved surface forms an unbroken curved line along a cross section that is parallel with the first leg and the second leg;

wherein each rounded depression that is in contact with and transitions from or to the adjacent rounded protrusion forms an unbroken S-shaped curve along a cross section that is parallel with the first leg and the second leg;

said plurality of alternating rounded protrusions and said plurality of alternating rounded depressions being arranged within the inside vessel engaging surfaces such that a portion of the vessel engaging surfaces remains a flat surface adjacent the protrusions and depressions; and wherein the protrusions of the first leg do not mesh into the depressions of the second leg when the clip is in a clamped or closed position.

9. The ligation clip of claim 8, further comprising transition edges between an outer surface thereof and multiple inside surfaces including the vessel engaging surface, said transition edges being rounded to a radius in a range of 0.003-0.006 inches so as to provide the ligation clip with no sharp edges.

\* \* \* \* \*